United States Patent [19]

Jones

[11] Patent Number: 6,106,578
[45] Date of Patent: *Aug. 22, 2000

[54] HAIR DYE COMPOSITIONS AND METHOD OF THICKENING THE SAME

[75] Inventor: Charles Elwood Jones, Yardley, Pa.

[73] Assignee: Rohm and Haas Company, Philadelphia, Pa.

[*] Notice: This patent issued on a continued prosecution application filed under 37 CFR 1.53(d), and is subject to the twenty year patent term provisions of 35 U.S.C. 154(a)(2).

[21] Appl. No.: 09/072,788

[22] Filed: May 6, 1998

[51] Int. Cl.$^7$ ...................................................... A61K 7/13
[52] U.S. Cl. ........................................ 8/406; 8/405; 8/552
[58] Field of Search ............................. 8/405, 406, 435, 8/552, 561, 562, 602, 611

[56] References Cited

U.S. PATENT DOCUMENTS

| | | | |
|---|---|---|---|
| Re. 33,786 | 1/1992 | Pohl et al. | 8/406 |
| 3,770,684 | 11/1973 | Singer | 524/306 |
| 3,811,830 | 5/1974 | DeMarco | 8/405 |
| 3,977,826 | 8/1976 | Iscowitz | 8/416 |
| 4,030,882 | 6/1977 | Blackwell | 8/657 |
| 4,079,028 | 3/1978 | Emmons et al. | 260/29.6 NR |
| 4,129,455 | 12/1978 | Thompson et al. | 106/308 N |
| 4,155,892 | 5/1979 | Emmons et al. | 260/29.2 TN |
| 4,426,485 | 1/1984 | Hoy et al. | 524/591 |
| 4,496,708 | 1/1985 | Dehm et al. | 528/76 |
| 4,499,233 | 2/1985 | Tetenbaum et al. | 524/591 |
| 4,507,426 | 3/1985 | Blake, Jr. | 524/505 |
| 4,776,855 | 10/1988 | Pohl et al. | 8/406 |
| 5,023,309 | 6/1991 | Kruse et al. | 528/49 |
| 5,100,658 | 3/1992 | Bolich, Jr. et al. | 8/405 |
| 5,104,646 | 4/1992 | Bolich, Jr. et al. | 8/405 |
| 5,106,609 | 4/1992 | Bolich, Jr. et al. | 8/405 |
| 5,281,654 | 1/1994 | Eisenhart et al. | 524/400 |
| 5,376,146 | 12/1994 | Casperson et al. | 8/408 |
| 5,393,305 | 2/1995 | Cohen et al. | 8/406 |
| 5,478,562 | 12/1995 | Cauwet et al. | 424/401 |
| 5,512,289 | 4/1996 | Tseng et al. | 424/426 |
| 5,685,882 | 11/1997 | Samain et al. | 78/406 |
| 5,716,418 | 2/1998 | Matzik et al. | 8/406 |
| 5,750,604 | 5/1998 | Banning et al. | 524/187 |
| 5,849,042 | 12/1998 | Lim et al. | 8/408 |
| 5,851,237 | 12/1998 | Anderson et al. | 8/409 |
| 5,865,854 | 2/1999 | Lim et al. | 8/408 |

FOREIGN PATENT DOCUMENTS

| | | |
|---|---|---|
| 1-93515 | 4/1989 | Japan . |
| 97/24106 | 7/1997 | WIPO . |
| 98/03150 | 1/1998 | WIPO . |

OTHER PUBLICATIONS

CFTA On–Line Home Page printout, "PEG–150/Decyl Alcohol/SMDI Copolymer." 1998 (No Month Available).

"A Study of the Interaction of Hydrophobically–Modified Polyols with Surfcants", C.E. Jones, Proceedings of the 4$^{th}$ World Surfactants Congress, Barcelona, 1996, vol. 2, pp. 439–450.

"Interfacial Phenomena", J.T. Davies, E.K. Rideal, 2$^{nd}$ Edition, 1963, pp. 370–445.

"Surfcants and Interfacial Phenomena" Milton J. Rosen, 1978, pp. 224–250.

"Surfactants in Consumer Products: Theory, Technology and Application", J. Falbe, 1986, pp. 86–87, 152–153, 174–175.

"Aculyn® 44 Cosmetic Grade Rheology Modifier and Stabilizer" Rohm and Haas Technical Bulletin FC–309, Jul. 1994.

"Aculyn® 46 Cosmetic Grade Rheology Modifier and Stabilizer" Rohm and Haas Technica Bulletin FC–404, May 1997.

*Primary Examiner*—Caroline D. Liott
*Attorney, Agent, or Firm*—Thomas J. Howell

[57] ABSTRACT

The present invention provides hair dye compositions containing a certain rheology modifying system. The hair dye compositions have improved thickening and shear thinning properties. The present invention also provides a method of thickening a hair dye composition using the rheology modifying system.

12 Claims, No Drawings

6,106,578

HAIR DYE COMPOSITIONS AND METHOD OF THICKENING THE SAME

FIELD OF INVENTION

The present invention relates to hair dye compositions which contain a rheology modifying system useful for providing to the compositions improved thickening and shear thinning properties. The present invention also relates to a method of thickening a hair dye composition.

BACKGROUND

Modern hair coloring techniques involve applying one or more formulations, such as a liquid, gel, paste or cream, containing one or more dyeing agents to the hair. The dyeing agents are left on the hair for a period of time, hereinafter referred to as the "color development period" to allow the dyeing agents to change the color of the hair. Dyeing agents useful in hair formulations include "permanent", "semipermanent", and "temporary" dyes.

Permanent dyes last through many washings and generally remain until the hair grows out. The most common type of permanent dye used today are oxidation dyes. When oxidation dyes are used, one or more dye precursors are combined with an oxidizing agent, such as hydrogen peroxide, before being applied to the hair. The dye precursors then react with the oxidizing agent to produce the dye within the hair. Because it is not desirable to produce the dye until after application on the hair, oxidation dyes are typically provided in two parts: a dye lotion containing the dye precursors, and a developer solution containing the oxidizing agent. The dye lotion and developer solution are then mixed shortly before application to the hair.

Semi-permanent dyes are generally removed from the hair after two to ten washings. Semi-permanent dyes are applied directly onto the hair, and are typically referred to as "direct dyes". In contrast to permanent dyes, semi-permanent do not use oxidizing agents to produce the dye. Direct dyes penetrate into the hair during the color development period, and slowly diffuse out of the hair when washed.

Temporary dyes, also known as color rinses, are typically removed from the hair after just one washing. These dyes, instead of penetrating into the hair as with semi-permanent dyes, deposit on the hair surface. The most common temporary hair dyes are water soluble acid dyes.

The hair dyeing formulations, in addition to containing the dyeing agents, also contain other additives to provide desirable performance properties. For example, the hair dye formulation should permit rapid diffusion of the dyeing agent into the hair. The hair dye formulation also needs to be readily rinseable after the color development period.

In addition, the rheological or flow properties of the hair dye formulation are important. For example, the hair dye formulation should be easily applied or spread onto the hair by brush or fingers to provide uniform coverage of the dyeing agents throughout the hair. Also, the hair dye formulation once applied should not drip or run off the hair during the color development period. The hair dye formulation should therefore be "shear thinning". Shear thinning means that as the formulation is subject to increasing shear, such as by applying the formulation to the hair by a brush, the viscosity of the formulation decreases. This decrease in viscosity upon shearing permits easy application of the formulation onto the hair. In addition to shear thinning, once the shear is removed, the viscosity of the hair dye formulation should recover or increase back to its original low shear rate viscosity. A rapid recovery of the viscosity prevents the hair dye composition from dripping or running after application to the hair.

In order to provide these rheological properties to hair dye formulations, rheology modifiers are added. However, a problem has been to find rheology modifiers that do not adversely react with other components in the formulation or adversely affect performance properties of the formulation. For example, in two part oxidation dye hair formulations, the developer solution typically contains hydrogen peroxide as an oxidizing agent. The hydrogen peroxide tends to react with other components added to the developer, such as a rheology modifier.

An additional problem with oxidation dye formulations has been that it is desirable to provide a dye lotion and developer solution which have low viscosities for mixing, preferably less than 5000 centipoises at low shear rates (Brookfield viscometer), but when mixed, thicken to provide the desired rheological properties.

U.S. Pat. No. 4,776,855 to Pohl, et.al, hereinafter referred to as "Pohl", discloses a two part oxidation hair dye formulation which uses as a thickener Acrysol-ICS (trademark of Rohm and Haas, presently supplied by Rohm and Haas as Aculyn 22). Acrysol-ICS is a hydrophobically modified acrylate copolymer which thickens at an aqueous pH greater than about 7. Pohl discloses adding the Acrysol-ICS to a developer solution having a pH of about 1.5 to 5.5. When the developer solution is combined with the dye lotion, the resulting hair dye formulation is thickened because the dye lotion is basic and adjusts the overall pH of the hair dye formulation to greater than 7.

However, the hair dye formulation in Pohl has several disadvantages. First, in order to maintain a low viscosity in both the dye lotion and developer solution, the Acrysol-ICS generally cannot be added to the dye lotion since the dye lotion typically has a pH greater than 7. Additionally, the dye lotion often contains cationic additives that would adversely react with Acrysol-ICS since Acrysol-ICS is anionic. Second, the rheology properties of the Pohl hair dye formulation, as detailed hereinafter, could be improved.

U.S. Pat. No. 4,079,028 to Emmons, et. al, hereinafter referred to as "Emmons", discloses certain polyurethanes. These polyurethanes are disclosed to be useful primarily in latex paints as rheology modifiers and thickeners. Emmons does not disclose the use of these polyurethanes in hair dye formulations, or disclose their use in combination with certain associating agents in hair dye formulations.

It is desirable to provide a hair dye composition which has improved shear thinning properties. It is also desirable to provide a hair dye composition which has improved resistance to dripping and running once applied to the hair. In addition, it is desirable to provide a hair dye composition where the rheology modifiers can be added to either the dye lotion or developer solution of an oxidation hair dye formulation. The present invention addresses this problem by incorporating into hair dye compositions a certain rheology modifying system.

STATEMENT OF THE INVENTION

The present invention provides a hair dye composition comprising: a) one or more hair dyeing agents; b) at least 0.1 weight percent of at least one hydrophobically modified nonionic polymer, based on the total weight of the hair dye composition, c) at least 0.1 weight percent of at least one associative agent, based on the total weight of the hair dye composition; and d) water.

In a second aspect of the invention a multi-part hair dye composition is provided comprising a) a dye lotion comprising one or more hair dyeing agents, and at least one first compound selected from the group consisting of a hydrophobically modified nonionic polymer, an associative agent, and combinations thereof, and b) a developer solution comprising at least one oxidizing agent, water, and at least one second compound selected from the group consisting of a hydrophobically modified nonionic polymer, an associative agent, and combinations thereof, and provided that when the parts of the multi-part hair dye composition are combined to form a combined hair dye composition, the combined hair dye composition comprises at least one hydrophobically modified nonionic polymer, and at least one associative agent.

In a third aspect of the invention a method of thickening a hair dyeing composition is provided comprising combining one or more hair dyeing agents, water, at least 0.1 weight percent of at least one hydrophobically modified nonionic polymer, and at least 0.1 weight percent of at least one associative agent to form the hair dye composition.

DETAILED DESCRIPTION

The present invention provides two hair dye compositions. The first hair dye composition is meant to include any formulation containing permanent, semi-permanent, or temporary dyeing agents, or combinations thereof which is applied to the hair. This first hair dye composition may be prepared in various ways. For example, the hair dye composition may be completely prepared at one time using a semi-permanent dye. The hair dye composition may also be prepared by mixing two or more parts together immediately before application to the hair, such as in a two part oxidative hair dye formulation.

The second hair dye composition of the present invention is meant to include the separate parts of a hair dye formulation which have not yet been combined for application on the hair. For example this second hair dye composition includes a composition comprising a dye lotion and developer solution which has not yet been combined.

As used herein "thicker", "thickened", or "thickening" means the increase in viscosity observed at a given shear rate on a Brookfield viscometer. A "low" shear rate refers to a shear rate of less than or equal to 0.3 rpm on a Brookfield viscometer. A "high" shear rate refers to a shear rate of greater than or equal to 30 rpm on a Brookfield viscometer.

At low shear rates, preferably, the hair dye composition which is applied to the hair has a Brookfield viscosity of at least 6000 centipoises (millipascal-seconds), more preferably at least 12,000 centipoises, and most preferably from 15,000 centipoises to 300,000 centipoises. At high shear rates, preferably the hair dye composition which is applied to the hair has a Brookfield viscosity of less than or equal to 6000 centipoises, more preferably less than or equal to 3000 centipoises, and most preferably less than or equal to 1000 centipoises.

The hair dye compositions of the present invention include a rheology modifying system containing at least one hydrophobically modified nonionic polymer (HNP) and at least one associative agent. The associative agent when combined with the hydrophobically modified nonionic polymer in the hair dye composition provides a thicker hair dye composition than what the hydrophobically modified nonionic polymer would provide without the associative agent in the hair dye composition. The associative agent when combined with the hydrophobically modified nonionic polymer in the hair dye composition also enhances the shear thinning properties of the hair dye composition in comparison to using the hydrophobically modified nonionic polymer without the associative agent.

These improvements in the rheological properties of the hair dye composition are related to the following performance benefits. First, the resistance of the hair dye composition to drip or run once applied to the hair is effected by the hair dye composition's viscosity at low shear rates. The higher the viscosity at a low shear rate, the greater the resistance of the composition to drip or run. Second, the ease in which the hair dye composition is applied to the hair is effected by the hair dye composition's viscosity at high shear rates. The lower the viscosity at a high shear rate, the easier the hair dye composition will be to apply.

The hydrophobically modified nonionic polymer (HNP) useful in the present invention preferably thickens by association, meaning that the HNP interacts or associates with itself and other components in hair dye compositions to provide thickening. The hair dye composition, as applied to the hair, preferably contains at least 0.1 weight percent, preferably from 0.1 weight percent to 15 weight percent, and more preferably from 0.2 weight percent to 5 weight percent HNP, based on the total weight of the hair dye composition applied to the hair and based on the HNP being 100 weight percent solid polymer.

The HNP contains at least one hydrophobic group. As used herein, the hydrophobic group is any chemical group that promotes water insolubility and includes, for example, alkyl, or aralkyl groups containing from about 4 to about 30 carbon atoms. Hydrophobic groups also include, for example, the hydrocarbon residues of hydroxyl, amino or isocyanate reactants, or any portion or segment of the polymeric reaction product that contributes to water insolubility. In addition, the HNP is nonionic which means it has no charge when dissolved or dispersed in aqueous solutions. Preferably, the HNP is water soluble or water swellable.

Suitable HNPs include for example polyethoxylated urethane, or hydrophobically modified naturally derived polyols such as a hydrophobically modified cellulose, or hydrophobically modified starch, or combinations thereof. The most preferred HNP is a polyethoxylated urethane.

The hydrophobically modified cellulose is a cellulose containing derivative which has been modified with at least one hydrophobic group. The hydrophobic groups are typically introduced by well known methods to functionalize some portion of the free hydroxyl groups in the cellulose polymer. Preferably, the hydrophobic group is a $C_4$ to $C_{20}$ alkyl or aralkyl group. Examples of hydrophobically modified celluloses useful in the present invention and methods of preparation include those described in U.S. Pat. Nos. 4,228,277, and 4,904,772. A preferred hydrophobically modified cellulose is a cetyl hydroxyethylcellulose.

The hydrophobically modified starch is a starch containing derivative which has been modified with at least one hydrophobic group. Preferably, the hydrophobic group is a $C_4$ to $C_{30}$ alkyl or aralkyl group. An example of a hydrophobically modified starch is Solanace™ which is supplied by National Starch.

The polyethoxylated urethane, hereinafter referred to as a "polyurethane" is a condensation polymer of at least one polyether polyol and at least one isocyanate.

The polyurethane contains hydrophobic groups which are linked by hydrophilic polyether groups. The hydrophobic groups may be located internally within the polymer, externally at the ends of the polymer, or both internally and externally. Preferably the polyurethane contains at least three hydrophobic groups. Additionally, the polyurethane preferably contains at least 20 carbon atoms, in total, in the hydrophobic portions of the polyurethane.

The polyurethane preferably has a weight average molecular weight (Mw) of from 10,000 to 200,000, more preferably from 12,000 to 150,000.

U.S. Pat. Nos. 4,079,028, 4,155,892, 4,426,485, 4,496,708, 4,499,233, 5,023,309, and 5,281,654 describe in detail compositions and methods for making the polyurethane which is useful in the hair dye compositions of the present invention. The polyurethane may have various structural shapes and may be for example linear, star shaped, or complex such as described in U.S. Pat. Nos. 4,079,028, and 4,155,892, or may be comb-shaped as in U.S. Pat. No. 4,496,708, or bunched as in U.S. Pat. No. 4,426,485.

Preferably, the polyurethane is prepared in a non-aqueous media and is the reaction product of at least reactants (a) and (c) or (a) and (b). The polyurethane may optionally include reactant (d). Reactants (a), (b), (c), and (d) are described as follows:

(a) at least one water-soluble polyether polyol;

(b) at least one water-insoluble organic polyisocyanate;

(c) at least one monofunctional hydrophobic organic compound selected from a monofunctional active hydrogen compound and an organic monoisocyanate; and (d) at least one polyhydric alcohol or polyhydric alcohol ether.

The hydrophilic polyether polyol, reactant (a), is water soluble and preferably has a Mw of at least 1500, more preferably at least 3000. The polyether polyol is typically an adduct of an aliphatic, cycloaliphatic, or aromatic polyhydroxy compound such as an adduct of an alkylene oxide and a polyhydric alcohol or polyhydric alcohol ether, a hydroxyl-terminated prepolymer of such adduct and an organic polyisocyanate, or a mixture of such adducts with such prepolymers.

A convenient source of the hydrophilic polyether polyol adducts is a polyalkylene glycol (also known as a polyoxyalkylene diol) such as polyethylene glycol, polypropylene glycol, or polybutylene glycol.

The organic polyisocyanate, reactant (b), may contain any number of carbon atoms effective to provide the required degree of hydrophobic character. Generally, about 4 to 30 carbon atoms are sufficient, the selection depending on the proportion of the other hydrophobic groups and hydrophilic polyether in the product. Suitable organic polyisocyanates include for example di- and triisocyanates, isocyanate-terminated adducts of such polyhydric alcohols and organic di- or triisocyanates, as well as isocyanate-terminated prepolymers of polyalkylene ether glycols and organic di- or triisocyanates. While it is preferred that reactant (b) be an organic polyisocyanate, reactants containing one or more functional groups other than isocyanate are also suitable.

Reactant (c), a monofunctional hydrophobic organic compound is a compound capable of reacting with one or both terminal functional groups of the reaction product of reactants (a) and (b). Reactant (c) includes both a monofunctional active hydrogen compound and an organic monoisocyanate.

The term "monofunctional active hydrogen compound" means an organic compound having only one group which is reactive with isocyanate, such group containing an active hydrogen atom, where any other functional groups, if present, being substantially unreactive to isocyanate. Such compounds include monohydroxy compounds such as alcohols, alcohol ethers, or alcohol polyethers; and monoamines; as well as polyfunctional compounds providing the compound is only monofunctional to isocyanates. The most preferred monofunctional active hydrogen compounds are $C_6$–$C_{25}$ straight or branched alcohols, alcohol ethers, or alcohol polyethers.

In addition to a monofunctional active hydrogen compound, reactant (c) may be a monoisocyanate. The monoisocyanate may include $C_6$ to $C_{18}$ straight chain, branched chain, and cyclic isocyanates such as for example, butyl isocyanate, octyl isocyanate, dodecyl isocyanate, octadecyl isocyanate, and cyclohexyl isocyanate. These isocyanates may be used singly or in mixtures of two or more thereof.

Reactant (d), a polyhydric alcohol or polyhydric alcohol ether, may be used for example to terminate isocyanate functionality or to link isocyanate-terminated reaction intermediates. The polyhydric alcohol or polyhydric alcohol ether may be aliphatic, cycloaliphatic or aromatic and may be used singly or in mixtures.

Further compounds which may be used as reactants (a), (b), (c), or (d) may be found in U.S. Pat. No. 4,079,028.

By appropriate selection of reactants and reaction conditions, including proportions and molecular weights of reactants, a variety of polymeric products may be obtained. Reaction products formed include the following:

(1) a reaction product of at least one water soluble polyether polyol reactant (a), a water insoluble organic polyisocyanate reactant (b), and an organic monoisocyanate reactant (c);

(2) a reaction product of the reactant (a), the reactant (b), the organic monoisocyanate reactant (c), and a reactant (d) selected from at least one polyhydric alcohol and polyhydric alcohol ether;

(3) a reaction product of the reactant (a), the water insoluble organic polyisocyanate reactant (b) containing two isocyanate groups, and an monofunctional active hydrogen containing compound reactant (c).

(4) a reaction product of the reactant (a), the water insoluble organic polyisocyanate reactant (b) containing two isocyanate groups, and a reactant (d) selected from at least one polyhydric alcohol or polyhydric alcohol ether.

A preferred polyurethane is a reaction product of at least one water soluble polyether polyol, such as polyethylene glycol, a water insoluble organic polyisocyanate, such as an organic diisocyanate, and a monofunctional active hydrogen compound, reactant (c), where the monofunctional active hydrogen compound terminates or "caps" the polyurethane at one or more ends.

The most preferred polyurethane in the present invention is a mixture of polyurethanes as described in U.S. Pat. No. 5,281,654. Generally, the polyurethanes in the mixture are characterized by their end groups The mixture of polyurethanes contains a first polyurethane with at least two end groups, where each end group comprises a terminal isocyanate and a polyether, hereinafter "polyether end group"; a second polyurethane with at least two end groups, where each end group comprises a terminal isocyanate group and a non-functional group, hereinafter "non-functional end group"; and a third polyurethane with at least two end groups, where one end group comprises the polyether end group and one other end comprises the non-functional end group. The end groups on the polyurethanes may be in any sequence and do not exclude the possibility that the polyurethanes contains additional end groups such as being branched or star-shaped.

Each of the polyurethanes in the mixture may be present in an amount ranging from about 5 to about 90 mole percent. The first polyurethane is more preferably present in the mixture in an amount ranging from about 8.3 to about 75 mole percent, and most preferably in an amount ranging from about 8.3 to about 25 mole percent. The second polyurethane is more preferably present in the mixture in an amount ranging from about 8.3 to about 75 mole percent, and most preferably in an amount ranging from about 25 to about 75 mole percent. The third polyurethane is more preferably present in the mixture in an amount ranging from about 16.7 to about 83.4 mole percent, and most preferably in an amount ranging from about 16.7 to about 50 mole percent.

The polyether end group is obtained from the reaction product of a terminal isocyanate and a polyether alcohol. For any end group that is the reaction product of a polyether alcohol and a terminal isocyanate, the polyether alcohol must have only one terminal hydroxyl moiety which can react with the terminal isocyanate so that the polyether end group cannot further polymerize or react after this reaction has occurred. The polyether alcohol includes alkyl and aryl polyether alcohols. These alcohols may be straight or branched ($C_1$–$C_{22}$) alkanol/ethylene oxide and alkyl phenol/ethylene oxide adducts. In addition, the polyether alcohol may also include alkanol/propylene oxide and alkyl phenol/propylene oxide adducts containing 1–250 propylene oxide groups. More preferred polyether alcohols include polyethylene glycol methyl ether and polypropylene glycol methyl ether. Most preferred polyether alcohols are polyethylene glycol methyl ethers with 15–50 ethylene oxide groups.

The non-functional end group is obtained from the reaction product of a terminal isocyanate and a reactant, so that this end group cannot further polymerize or participate in any further reactions once this reaction has occurred. The reactant may be for example an alcohol, amine, acid, or mercaptan. It is preferred that the reactant is monofunctional in that it only has one group containing a hydrogen atom that can react with the terminal isocyanate group such as, for example, a monofunctional alcohol, monofunctional amine, monofunctional acid, or monofunctional mercaptan. Preferably, the reactant is a monofunctional alcohol.

It is preferable that the Mw, of the polyether alcohol is greater than 500. It is also preferable that the weight average molecular weight, Mw, of the reactant, such as, for example, the monofunctional alcohol, monofunctional amine, monofunctional mercaptan, monofunctional acid, and the like, is less than 500. Further examples of polyether alcohols and reactants are described in U.S. Pat. No. 5,281,654.

The polyurethane mixtures are prepared by techniques disclosed in U.S. Pat. No. 5,281,654. The polyurethanes in the mixture can be prepared individually and then blended. However, it is preferred to prepare the polyurethane mixture in a one step process whereby all three polyurethanes are prepared simultaneously in the same reactor.

The polyurethane mixtures are preferably a reaction product of an organic diisocyanate; a polyether polyol, such as, for example, polyethylene glycol, polyether alcohol, and at least one reactant such as an alcohol, amine, acid, or mercaptan. The molar ratio of polyol to diisocyanate preferably ranges from 1:1.01 to 1:5, more preferably from 1:1.01 to 1:3. The moles of polyether alcohol and reactant are preferably at least two times greater than the difference between the moles of diisocyanate and polyol. The molar ratio of polyether alcohol to the reactant is preferably from 10:1 to about 1:10, and more preferably from 1:1 to 1:5. The percent of each type of polyurethane in the mixture may be varied by changing the molar ratio of the polyether alcohol and reactant.

In addition to the HNP, the rheology modifying system useful in the present invention contains at least one associative agent. The associative agent is present in the hair dye composition preferably at a concentration of at least 0.1 weight percent, more preferably from 1.0 to 25 weight percent, and most preferably from 5 to 20 weight percent based on the total weight of the hair dye composition applied to the hair.

The associative agent contains at least one hydrophilic and at least one hydrophobic group which interacts with the HNP to provide thickening and shear thinning properties. The associative agent preferably has an average hydrophilic-lipophilic balance (HLB) of 15 or less, more preferably 12 or less, and most preferably 11 or less. "Average HLB" as used herein is determined according to Equation 1:

$$HLB_{avg} = \Sigma w_i \times HLB_i \qquad \text{Equation 1}$$

where $HLB_{avg}$ is the average HLB of all associative agents in the rheology modifying system, $w_i$ is the weight fraction of associative agent, where all weight fractions of the associative agents add up to 1, and $HLB_i$ is the HLB of associative agent i.

HLB is a value characterizing the relative proportions of hydrophilic and lipophilic (i.e., hydrophobic) portions of molecules. Higher HLB values (those approaching 40) represent more hydrophilic molecules and lower HLB values (those around 6 to 10) represent more hydrophobic molecules. HLB values may be calculated or determined experimentally by a variety of known procedures, such as those described in "Surfactants and Interfacial Phenomena" by Milton J. Rosen, John Wiley and Son, New York, N.Y., page 242–244 (1978) and "Interfacial Phenomena" by J. T. Davies and E. K. Rideal, Academic Press, 2nd Edition, pp 373–383 (1963). The HLB values used herein are based on the calculation of the hydrophilic content of the associative agent and were obtained from the supplier of the associative agent. Where an HLB value is not supplied by the manufacturer, the 1949 calculation method by Griffin disclosed in "Surfactants and Interfacial Phenomena" can be used.

In addition to the HLB, the associative agent preferably has a total of at least 6 carbon atoms, more preferably from 8 to 30 carbon atoms and most preferably from 10 to 25 carbon atoms in all hydrophobic groups in the associative agent.

The associative agent useful in the present invention is typically a surfactant. The associative agent may be nonionic, anionic, cationic, or amphoteric. Additionally, combinations of more than one type of associative agent may be used. For example the rheology modifying system may contain mixtures of nonionic with anionic, nonionic with cationic, nonionic with amphoteric, anionic with amphoteric, and cationic with amphoteric associative agents as long as they are compatible with the other ingredients in the hair dye composition.

Nonionic associative agents have no charge when dissolved or dispersed in aqueous solutions. Typical nonionic associative agents useful in the present invention include, for example, ($C_6$–$C_{18}$)alkylphenol alkoxylates (such as t-octyl phenol and nonylphenol ethoxylates having 1–70, and preferably 5–16, ethyleneoxide units), ($C_{12}$–$C_{20}$)alkanol alkoxylates and block copolymers of ethylene oxide and propylene oxide; optionally, the end groups of polyalkylene oxides can be blocked, whereby the free OH groups of the polyalkylene oxides can be etherified, esterified, acetalized and/or aminated. Another modification consists of reacting the free OH groups of the polyalkylene oxides with isocyanates. Useful nonionic associative agents also include, for example, ($C_4$–$C_{18}$)alkyl glucosides as well as the alkoxylated products obtainable therefrom by alkoxylation, particularly those obtainable by reaction of alkyl glucosides with ethylene oxide.

Anionic associative agents have a hydrophilic functional group in a negatively charged state in an aqueous solution. Typical anionic associative agents useful in the present invention include, for example, ($C_8$–$C_{18}$)alkyl carboxylic acids, ($C_{12}$–$C_{20}$)sulfonic acids (sulfonated alkylaryl compounds such as sodium dodecylbenzenesulfonate), ($C_{10}$–$C_{20}$)sulfuric acid esters (sulfated alcohols such as lauryl and cetyl sulfates, sodium salts), phosphate esters and salts thereof.

Cationic associative agents have hydrophilic functional groups where the charge of the functional groups is positive when dissolved or dispersed in an aqueous solution. Typical cationic associative agents useful in the present invention include, for example, ($C_{12}$–$C_{20}$)amine compounds (such as lauryl pyridinium chloride, octylbenzyltrimethylammonium chloride and dodecyltrimethylammonium chloride), oxygen containing amines, quaternary amine salts, or polyquaternary compounds such as Polyquaternium-4, or Polyquaternium-10 (CTFA names); or combinations thereof.

Amphoteric or zwitterionic associative agents contain both acidic and basic hydrophilic groups and can be used in the present invention. Examples of amphoteric associative agents include betaines, such as cocamidopropylbetaine, sultaines, proprionates, or glycinates. Further examples of amphoteric associative agents are disclosed in U.S. Pat. 5,376,146.

In addition to associative agents described so far, the associative agent may be a polysilicone, fatty acid, or $C_8$–$C_{25}$ alcohol.

Generally, a nonionic associative agent, such as an alcohol ethoxylate or alkylphenol ethoxylate is preferred for use in the present invention. More preferably, mixtures of nonionic associative agents are used. The most preferred associative agent is a mixture of alkylphenol ethoxylates, alcohol ethoxylates, or combinations thereof.

In addition to the rheology modifying system, the hair dye compositions contain one or more dyeing agents. The dyeing agents include for example permanent, semi-permanent, or temporary dyes, or combinations thereof. As used herein, dyeing agents are meant to include dye precursors which when reacted with another reactant, such as an oxidizing agent, forms a dye. For example, dyeing agents include primary or secondary intermediates useful in two part oxidative hair dye formulations. Preferably, the hair dye compositions contain at least 0.0001 weight percent, more preferably from 0.001 to 2.0 weight percent, and most preferably from 0.01 to 1.0 weight percent total dyeing agents, based on the total weight of the hair dye composition which is applied to the hair. The selection and amount of the dyeing agents chosen depends on the desired hair color.

As previously mentioned herein the most common type of permanent dye is an oxidation dye. The oxidation dye is formed through the reaction of at least one primary intermediate, at least one secondary intermediate also referred to as a coupler or modifier, and at least one oxidizing agent.

Primary intermediates include for example para dyes such as unsubstituted or substituted p-phenylenediamine, p-toluenediamine, p-aminodiphenylamine, or p-aminophenol, or combinations thereof. Primary intermediates may also be ortho bases such as ortho-aminophenol, 5-chloro-orthoaminophenol, or orthophenylenediamine or combinations thereof.

The secondary dye intermediates, also referred to as couplers include for example m-phenylenediamines, m-aminophenols, polyhydroxyphenols, resorcinol, or napthols, or combinations thereof.

The oxidizing agent oxidizes the primary and secondary intermediates to produce a dye within the hair. A typical oxidizing agent is for example hydrogen peroxide. The oxidizing agent may also be for example urea peroxide, melamine peroxide, perborates, or percarbonates or combinations thereof.

Further examples of primary intermediates, secondary intermediates, and oxidizing agents are found in U.S. Pat. No. 5,376,146.

Other examples of permanent dyes, in addition to oxidation dyes, include for example nitro dyes such as nitro derivatives of aminophenols or benzenediamines; or autooxidation dyes such as 1,2,4,-trisubstituted benzenes; or combinations thereof. Preferably, the permanent dye used is an oxidation dye.

Semipermanent dyes include for example direct dyes. Suitable direct dyes include for example nitro compounds such as nitrophenylenediamines, nitroaminophenols, or anthraquinone dyes; or azobenzenes; or combinations thereof. Metal complex dyes or premetallized dyes can also be used as semi-permanent dyes.

Temporary dyes include anthraquinone, azo, disazo, nitro, and phenylmethane dye types. Basic dyes, such as methylene blue, rhodamine, or methyl violet, or combinations thereof may also be use as temporary dyes.

Further examples of permanent, semi-permanent, and temporary dyes are found in the International Cosmetic Ingredients Dictionary, 5th Edition, 1993, published by the CTFA in Washington D.C.

The hair dye composition in addition to containing the rheology modifying system and one or more dyeing agents preferably contains at least 50 weight percent water, more preferably from 55 to 90 weight percent water, and most preferably from 65 to 85 weight percent water, based on the total weight of the hair dye composition applied to the hair.

The pH of the hair dye composition which is applied to the hair is preferably from 6 to 12 and more preferably from 8 to 10. The pH of the hair dye composition may be adjusted by such additives as alkali metal or ammonium hydroxide; or amines such as 2-amino-2-methyl propanediol, 2-amino-2-methylpropanol, N,N-dimethyl-2-amino-2-methyl-1-propanol, monoisopropanolamine, triisopropanolamine, ethanolamine, triethanolamine, or morpholine; or combinations thereof.

The hair dye composition is meant to include any liquid composition useful for dyeing hair such as a gel, lotion, cream, or paste. Preferably the hair dye composition has a solids content of 50 weight percent or less and more preferably from 10 to 45 weight percent, based on the total weight of the hair dye composition applied to the hair.

The hair dye composition applied to the hair may be formed by combining all ingredients at one time. Although the order of addition is not critical, it is preferred to heat a portion or all of the water to a temperature of around 40° C. to 50° C. and then add the at least one associative agent. After adding the associative agent, the other ingredients can be added in no preferable order.

In a preferred embodiment of the present invention, the hair dye compositions use as the dyeing agents one or more oxidation dyes. When oxidation dyes are used, preferably a multi-part hair dye composition (an example of the second hair dye composition of this invention), is prepared. The parts of the multi-part hair dye composition are then mixed immediately before application to the hair to form the first hair dye composition. This multi-part hair dye composition is typically provided in a kit, ready for mixing by the user. When the parts are mixed, the resulting hair dye composition has the desired rheology so that the composition is easy to apply and does not drip or run.

Typically, one part of a multi-part hair dye composition is a dye lotion, and a second part of the multi-part hair dye composition is a developer solution. Preferably the weight ratio of the dye lotion to developer solution is from 25:75 to 75:25 and more preferably is from 40:60 to 60:40. In order to enhance mixing of the parts, it is preferable that each part have a Brookfield viscosity equal or less than 6000 centipoises, and more preferably equal to or less than 1000 centipoises.

The dye lotion contains one or more dyeing agents as previously defined herein, and at least one first compound selected from the HNP, the associative agent or combinations thereof. The dye lotion preferably has a pH equal to or greater than 7, more preferably equal to or greater than 8. The dye lotion must also have sufficient alkalinity so that when the developer solution is combined with the dye lotion, the pH is maintained at a pH of 7 or greater, so that the reaction of the dye precursors and oxidizing agents is maintained.

The concentrations of the components in the dye lotion are as follows. The total concentration of the dyeing agents is preferably at a level of from 0.001 weight percent to 4 weight percent and more preferably from 0.01 weight percent to 1 weight percent based on the total weight of the dye lotion. The HNP if present in the dye lotion is preferably at a concentration of from 0.1 weight percent to 20 weight percent more preferably from 0.4 weight percent to 10 weight percent based on the total weight of the dye lotion and based on the HNP being 100 weight percent solid polymer. The associative agent if present in the dye lotion is preferably at a concentration of from 0.1 weight percent to 50 weight percent and more preferably from 1 weight percent to 30 weight percent, based on the total weight of the dye lotion.

The developer solution contains at least one oxidizing agent, water, and at least one second compound selected from the HNP, the associative agent, or combinations thereof. The developer solution preferably has a pH from 2 to 6, and more preferably a pH from 2.5 to 5.

The concentrations of the components in the developer solution are as follows. The oxidizing agent is preferably at a level of from 0.5 to 40 weight percent and more preferably from 0.5 to 30 weight percent based on the total weight of the developer solution. The HNP, if present in the developer solution, is preferably at a concentration of from 0.1 weight percent to 20 weight percent, more preferably from 0.4 weight percent to 10 weight percent, based on the total weight of the developer solution and based on the HNP being 100 weight percent solid polymer. The associative agent in the developer solution is preferably at a concentration of from 0.1 weight percent to 50 weight percent and more preferably from 1 weight percent to 30 weight percent, based on the total weight of the developer solution.

An advantage to the use of the HNP in a multi part hair dye composition is that the HNP can be added to either the dye lotion or developer solution without adversely affecting the other ingredients or significantly increasing the viscosity of either the dye lotion or developer solution. Preferably, the HNP is added to the dye lotion.

In a multi-part hair dye composition, it is preferred for full thickening efficiency that at least 70 percent, and more preferably all of the HNP is added to one part. Additionally, it is preferred that an associative agent which has an HLB of about 12 or less, should be added to a part not containing the HNP to prevent the part containing the HNP from significantly increasing in viscosity. However, it is possible as detailed hereinafter, to add associative agents having an HLB greater than or equal to about 13 to the part containing the HNP without significant thickening of the part. When associative agents are added to the part containing the HNP, it is preferred that the amount added be about 10 percent by weight or less, based on the total amount of associative agent.

In addition to the HNP, associative agent, and dyeing agents, other additives may be added to the hair dye compositions to enhance the properties of the composition. In total, these additive comprise from 0.5 weight percent to 15 weight percent and more preferably from 1 weight percent to 10 weight percent, based on the total weight of the hair dye composition applied to the hair. These additives include for example solvents, conditioners, wetting agents, antioxidants, electrolytic buffers, pH adjusters, chelating agents, or fragrances or combinations thereof. Solvents include for example alcohols containing up to 4 carbon atoms, polyhydroxy alcohols, or lower alkyl ethers such as ethoxy ethers. Conditioners include cationic or amphoteric compounds such as cocamidopropylbetaine, or polyquaternary compounds such as Polyquaternium-4, or Polyquaternium-10. Suitable wetting agents include for example anionic compounds such as sodium lauryl sulfate and suitable antioxidants include for example sodium sulfite. Further examples of suitable additives are found in the International Cosmetic Ingredients Dictionary, 5th Edition, 1993, published by the CTFA in Washington D.C.

EXAMPLES

Some embodiments of the invention will now be described in detail. Two part oxidative hair dye compositions were prepared to demonstrate the effectiveness of the HNP and associative agent in improving the rheology properties of hair dye compositions. The viscosities in Examples 1–23 and 25 were measured with a Brookfield DV-III viscometer, spindle number 4. Abbreviations and information on components used in the hair dye formulations in Tables 1–8 are presented in Table 9.

The hair dye compositions in Examples 1–25 were prepared by separately preparing the dye lotion and developer solution according to the compositions shown in Tables 2–8. The dye lotion was prepared by heating the water to around 45° C., and with mixing adding the other components. The developer solution was prepared by first heating the water to around 45° C. and then adding the one or more associative agents, followed by the remaining components. After each part was cooled to room temperature, the dye lotion and developer solution were combined in equal amounts and then shaken to provide the hair dye composition. The viscosity of the hair dye composition was measured immediately after combining the two parts.

In Examples 1–24 (Tables 2–7), the HNPs tested (Polymers A–E) were polyurethanes. Polymer A was prepared as follows:

To a one liter flask was added 195 grams of a polyethylene glycol of approximate molecular weight 8,000, 325 grains of toluene, and 0.2 grams of dibutyltin dilaurate. The mixture was azeotropically dried by refluxing the mixture and collecting any water in a Dean-Stark trap, cooled to 80° C., and 8.2 grams of methylene bis(4-cyclohexyl isocyanate) was added. After 2.5 hours, a mixture of 4.7 grams of 1-octadecanol and 11.5 grams of a polyethylene glycol methyl ether of approximate molecular weight 2,000 was added. The mixture was held at 80° C. for 4 hours and then cooled. The solid product was isolated by evaporation of the toluene.

Polymers B–E are condensation polymers of polyethylene glycol and diisocyanate. The hydrophobes for polymers B–E are listed in Table 1.

TABLE 1

Hydrophobes for Polyurethanes

| Polymer | Hydrophobe |
|---|---|
| B | $C_6$ hydrophobe |
| C | $C_{15}$ hydrophobe |
| D | $C_{10}$ hydrophobe |
| E | $C_{18}$ hydrophobe and $C_{12}$ hydrophobe |

Table 2 shows the hair dye composition of the present invention formulated to contain various polyurethanes. For all examples in Table 2, except for example 3 and comparative examples 1 and 2, the developer solution was prepared without hydrogen peroxide for easier handling. Example 4, which is identical to example 3 except for the absence of hydrogen peroxide, shows that the removal of hydrogen peroxide from the developer does not significantly effect the viscosity of the final hair dye composition. The polyurethanes shown in Table 2 were formulated into the hair dye composition at concentrations ranging from 0.25 weight percent to 2.5 weight percent, where the percentages are calculated based on the total weight of the hair dye composition and on the polyurethane being 100% polymer solids.

Table 2 shows the polyurethane can be formulated into the dye lotion part of a two part hair dye composition to provide a desirable final viscosity after the two parts are mixed. Table 2 also shows that examples 3–12, which use a polyurethane, are more effective in increasing the viscosity of a hair dye composition at low shear rates in comparison to comparative examples 1 and 2, which use a carboxylate polymer as the thickener. Comparative example 1, is similar to the example shown in U.S. Pat. No. 4,776,855 which uses for the lotion, formulation number 6, and uses for the developer, formulation B.

TABLE 2

Hair Dye Composition Containing Various Polyurethanes

| Components | C1[1] | C2[1] | 3 | 4 | 5 | 6 | 7 | 8 | 9 | 10 | 11 | 12 |
|---|---|---|---|---|---|---|---|---|---|---|---|---|
| Dye Lotion | (parts by weight) | | | | | | | | | | | |
| phenyldiamine | 0.50 | 0.50 | 0.50 | 0.50 | — | — | — | — | — | — | — | — |
| resorcinol | 0.50 | 0.50 | 0.50 | 0.50 | — | — | — | — | — | — | — | — |
| sodium sulfite | 0.10 | 0.10 | 0.10 | 0.10 | 0.10 | 0.10 | 0.10 | 0.10 | 0.10 | 0.10 | 0.10 | 0.10 |
| hexylene glycol | 2.00 | 2.00 | 2.00 | 2.00 | 2.00 | 2.00 | 2.00 | 2.00 | 2.00 | 2.00 | 2.00 | 2.00 |
| butyl carbitol | 4.00 | 4.00 | 4.00 | 4.00 | 4.00 | 4.00 | 4.00 | 4.00 | 4.00 | 4.00 | 4.00 | 4.00 |
| ammonia (28%) | 5.77 | 5.77 | — | — | — | — | — | — | — | — | — | — |
| $NH_4Cl$ | 2.84 | 2.84 | — | — | — | — | — | — | — | — | — | — |
| ethanolamine | — | — | 4.00 | 4.00 | 4.00 | 4.00 | 4.00 | 4.00 | 4.00 | 4.00 | 4.00 | 4.00 |
| Amphosol CA | — | — | 5.00 | 5.00 | 5.00 | 5.00 | 5.00 | 5.00 | 5.00 | 5.00 | 5.00 | 5.00 |
| SLS | 6.67 | 6.67 | — | — | — | — | — | — | — | — | — | — |
| sodium chloride | 0.10 | 0.10 | — | — | 0.10 | 0.10 | 0.10 | 0.10 | 0.10 | 0.10 | 0.10 | 0.10 |
| Triton N-401 | — | — | — | — | — | — | — | — | — | — | — | 1.00 |
| Neodol 25-12 | — | — | — | — | 1.00 | 1.00 | 1.00 | 1.00 | 1.00 | 1.00 | 1.00 | — |
| Polymer A | — | — | 1.00 | 1.00 | — | — | 0.50 | 1.00 | — | — | — | — |
| Polymer C | — | — | — | — | — | — | — | — | 0.50 | 1.00 | — | — |
| Polymer D | — | — | — | — | — | — | — | — | — | — | 1.00 | — |
| Polymer B | — | — | — | — | 1.00 | 5.00 | — | — | — | — | — | — |
| Polymer E | — | — | — | — | — | — | — | — | — | — | — | 1.00 |
| water | 77.52 | 77.52 | 77.23 | 77.23 | 78.80 | 58.80 | 80.47 | 77.13 | 80.94 | 78.09 | 80.94 | 82.80 |
| Developer | (parts by weight) | | | | | | | | | | | |
| $H_2O_2$, 50% | 10.00 | 10.00 | 10.00 | 0.00 | — | — | — | — | — | — | — | — |
| EDTA | 0.02 | 0.02 | 0.10 | 0.10 | — | — | — | — | — | — | — | — |
| Triton N-101 | — | — | — | — | — | — | — | — | — | — | — | 10.00 |
| Triton N-42 | — | — | — | — | — | — | — | — | — | — | — | 10.00 |
| Neodol 45-7 | | | 10.00 | 10.00 | 10.00 | 10.00 | 10.00 | 10.00 | 10.00 | 10.00 | 10.00 | — |
| Neodol 25-3 | | | 10.00 | 10.00 | 10.00 | 10.00 | 10.00 | 10.00 | 10.00 | 10.00 | 10.00 | — |
| Aculyn 22 | 10.00 | — | — | — | — | — | — | — | — | — | — | — |
| Aculyn 33 | — | 10.00 | — | — | — | — | — | — | — | — | — | — |
| water | 79.98 | 79.98 | 69.90 | 79.90 | 80.00 | 80.00 | 80.00 | 80.00 | 80.00 | 80.00 | 80.00 | 80.00 |
| Viscosity, cps | | | | | | | | | | | | |
| 0.3 rpm | — | — | 90000 | 91200 | 12000 | 20000 | 9333 | 24667 | 8667 | 12000 | 18000 | 48667 |
| 3 rpm | 1000 | 133 | 14120 | 15880 | 2400 | 3933 | 2000 | 4200 | 1800 | 2867 | 3933 | 12900 |
| 30 rpm | 620 | 33 | 5627 | 5907 | 613 | 1107 | 487 | 873 | 573 | 793 | 1287 | 3933 |

[1]Comparative

Table 3 shows the hair dye composition of the present invention can be prepared to provide a desirable viscosity when the polyurethane is formulated into the developer part of a two part hair dye composition. Table 3 also shows the effective use of various associative agents, including non-ionic and cationic associative agents.

TABLE 3

Hair Dye Composition Containing Polyurethane in Developer

| Components | 13 | 14 | 15 | 16 |
|---|---|---|---|---|
| Dye Lotion | (parts by weight) | | | |
| sodium sulfite | 0.10 | 0.10 | 0.10 | 0.10 |
| hexylene glycol | 2.00 | 2.00 | 2.00 | 2.00 |
| butyl carbitol | 4.00 | 4.00 | 4.00 | 4.00 |
| ethanolamine | 4.00 | 4.00 | 4.00 | 4.00 |
| Behenyltrimethyl ammonium chloride, 68% | 2.94 | 2.21 | 2.21 | 4.41 |
| sodium chloride | 0.10 | 0.10 | 0.10 | 0.10 |
| Triton N-401 | | | | 3.00 |
| Triton N-42 | | 10.00 | | 10.00 |
| Neodol 25-12 | 10.00 | | | |
| Neodol 45-7 | | | 10.00 | |
| Neodol 25-3 | | | 10.00 | |
| water | 76.86 | 77.59 | 67.59 | 72.39 |
| Developer | (parts by weight) | | | |
| Triton N-401 | | 1.00 | | 1.00 |
| Triton N-101 | | 10.00 | | |
| Neodol 25-12 | | | 1.00 | |
| Neodol 45-13 | 1.00 | | | |
| Polymer A | 1.00 | 1.00 | 1.00 | 1.00 |
| water | 92.33 | 82.33 | 92.33 | 92.33 |
| Viscosity, cps | | | | |
| 0.3 rpm | — | 6667 | 20000 | 13333 |
| 3 rpm | 133 | 1933 | 4000 | 3267 |
| 30 rpm | 13 | 620 | 1187 | 1067 |

Table 4 shows the effect of the associative agent's HLB on hair dye composition viscosity. Table 4 shows that formulations containing associative agents with an average HLB of around 11.6 results in a hair dye composition which is less viscous than a composition containing associative agents having an average HLB of around 10.5. In addition, examples 22 and 23 in Table 4 can be compared to examples 9 and 11 respectively in Table 1. Examples 9 and 11 each had an average HLB of around 10.0, whereas examples 22 and 23 each had an average HLB of around 11.6. Examples 9 and 11, which differed only in associative agent from examples 22 and 23 respectively, had a higher hair dye composition viscosity than examples 22 and 23.

TABLE 4

Effect of Associative Agent on Hair Dye Composition Viscosity

| Components | 17 | 18 | 19 | 20 | 21 | 22 | 23 |
|---|---|---|---|---|---|---|---|
| | (parts by weight) | | | | | | |
| sodium sulfite | 0.10 | 0.10 | 0.10 | 0.10 | 0.10 | 0.10 | 0.10 |
| hexylene glycol | 2.00 | 2.00 | 2.00 | 2.00 | 2.00 | 2.00 | 2.00 |
| butyl carbitol | 4.00 | 4.00 | 4.00 | 4.00 | 4.00 | 4.00 | 4.00 |
| ethanolamine | 4.00 | 4.00 | 4.00 | 4.00 | 4.00 | 4.00 | 4.00 |
| Amphosol CA, 30% | 5.00 | 5.00 | 5.00 | 5.00 | 5.00 | 5.00 | 5.00 |
| sodium chloride | 0.10 | 0.10 | 0.10 | 0.10 | 0.10 | 0.10 | 0.10 |
| Triton ® N-401 | 1.00 | 1.00 | 1.00 | 1.00 | 1.00 | 1.00 | 1.00 |
| Polymer A | 0.50 | 0.50 | 1.00 | 1.00 | | | |
| Polymer C | | | | | 1.00 | 0.50 | |
| Polymer D | | | | | | | 1.00 |
| water | 80.47 | 80.47 | 77.13 | 77.13 | 78.09 | 80.94 | 80.94 |
| Developer | (parts by weight) | | | | | | |
| Triton N-101 | 10.00 | 5.00 | | 5.00 | | 10.00 | 10.00 |
| Triton N-42 | 10.00 | 15.00 | | 15.00 | | 10.00 | 10.00 |
| Neodol 45-7 | | | 10.00 | | 10.00 | | |
| Neodol 25-3 | | | 10.00 | | 10.00 | | |
| water | 80.00 | 80.00 | 80.00 | 80.00 | 80.00 | 80.00 | 80.00 |
| Average HLB | 11.6 | 10.5 | 10.2 | 10.5 | 10.2 | 11.6 | 11.6 |
| Viscosity, cps | | | | | | | |
| 0.3 rpm | 7333 | 126000 | 18000 | 246000 | 38000 | 4000 | 12000 |
| 3 rpm | 1600 | 37533 | 3600 | | 7400 | 1133 | 2200 |
| 30 rpm | 420 | 4400 | 860 | | 1753 | 360 | 627 |

The average HLB for each example in Table 4 was calculated using Equation 1. Table 5 shows the HLB value used for each associative agent. Each HLB value was obtained from the manufacturer's literature.

TABLE 5

HLB Values

| Associative Agent | HLB |
|---|---|
| Neodol 25-12 | 14.4 |
| Neodol 25-3 | 7.8 |
| Neodol 45-13 | 14.5 |
| Neodol 45-7 | 11.8 |
| Triton N-101 | 13.4 |
| Triton N-401 | 17.8 |
| Triton N-42 | 9.1 |

A two part hair dye composition was prepared to evaluate the recovery the hair dye composition's viscosity with time after being subjected to increasing shear rates. The two part hair dye composition shown in Table 6 was prepared according to the procedure used for preparing examples 1–23.

TABLE 6

Hair Dye Composition- Example 24

| Components | parts by weight |
|---|---|
| Dye Lotion | |
| sodium sulfite | 0.5 |
| ethanolamine | 4.00 |
| Amphosol ® CA | 5.00 |
| Triton ® N-401 | 0.10 |
| Polymer A | 1.00 |
| water | 83.8 |
| Viscosity, 5 rpm, spindle #5 | 20 cps |
| Developer | |
| Water | 67.9 |
| $H_2O_2$, 50% | 12.0 |
| Neodol ® 45-7 | 10.0 |
| Neodol 25-3 | 10.0 |
| Phosphoric acid (85 wt %) | 0.1 |
| Viscosity, 5 rpm, spindle #5 | 507 cps |

After the dye lotion was combined with the developer, the viscosity of the resulting hair dye composition was measured over time while increasing and then decreasing the shear rate. The viscosity measurements in Table 7 were taken with a Brookfield DV-III viscometer, spindle number 5. The viscosity measurements obtained are shown in Table 7.

The data in Table 7 shows that example 24 recovered in viscosity, as the shear rate was decreased, after being subjected to increasing shear rates. This effect in rheology is desirable so that after the hair dye composition is applied, with shear, to the hair, the hair dye composition rapidly increases in viscosity to avoid dripping or running.

TABLE 7

Viscosity Measurements Versus Time for Example 24

| Time | RPM | Viscosity |
|---|---|---|
| 1:00 | 0.1 | 172,000 |
| 2:00 | 1.0 | 90,000 |
| 3:00 | 10.0 | 14,120 |

TABLE 7-continued

Viscosity Measurements Versus Time for Example 24

| Time | RPM | Viscosity |
|---|---|---|
| 4:00 | 30.0 | 5627 |
| 5:00 | 60.0 | 3,133 |
| 6:00 | 30.0 | 5,987 |
| 7:00 | 10.0 | 16,200 |
| 8:00 | 1.0 | 105,200 |
| 9:00 | 0.1 | 324,000 |

Table 8 shows that a hydrophobically modified cellulose is effective in providing thickening and shear thinning properties to a hair dye composition. In Table 8, Natrosol Plus 330, supplied by Aqualon, is cetyl hydroxyethyl cellulose.

TABLE 8

Hair Dye Composition Containing Hydrophobically Modified Cellulose

| Components | 25 |
|---|---|
| Dye Lotion | (parts by weight) |
| sodium sulfite | 0.10 |
| hexylene glycol | 2.00 |
| butyl carbitol | 4.00 |
| ethanolamine | 4.00 |
| Amphosol CA | 5.00 |
| sodium chloride | 0.10 |
| Triton N-401 | 1.00 |
| Neodol 25-12 | — |
| Natrosol Plus 330 | 1.00 |
| water | 76.86 |
| Developer | (parts by weight) |
| Triton N-101 | 10.00 |
| Triton N-42 | 10.00 |
| Neodol 45-7 | — |
| Neodol 25-3 | — |
| water | 80.00 |
| Viscosity, cps | |
| 0.3 rpm | 13,333 |
| 3 rpm | 3533 |
| 30 rpm | 1060 |

TABLE 9

Abbreviations

| Abbreviation/Component | Meaning |
|---|---|
| Aculyn 22 | trademark and supplied by Rohm and Haas, Acrylates/steareth 20 methacrylate copolymer |
| Aculyn 33 | trademark and supplied by Rohm and Haas, Acrylates copolymer |
| Amphosol CA, 30% | trademark and supplied by Stepan, cocamidopropylbetaine |
| butyl carbitol | trademark and supplied by Union Carbide |
| Neodol 25-12 | trademark and supplied by Shell $C_{12}$–$C_{15}$ alcohol ethoxylate (12 ethoxylate groups/molecule) |
| Neodol 45-13 | $C_{14}$–$C_{15}$ alcohol ethoxylate (13 ethoxylate groups/molecule) |
| Neodol 45-7 | $C_{14}$–$C_{15}$ alcohol ethoxylate (7 ethoxylate groups/molecule) |
| Neodol ® 25-3 | $C_{12}$–$C_{15}$ alcohol ethoxylate (3 ethoxylate groups/molecule) |
| phenyldiamine | p-phenylene diamine |
| SLS | sodium lauryl sulfate, 30 wt % solids |

TABLE 9-continued

Abbreviations

| Abbreviation/Component | Meaning |
|---|---|
| Triton N-101 | trademark and supplied by Union Carbide, nonylphenol ethoxylate ether (9–10 ethoxylate groups/molecule) |
| Triton N-401 | nonylphenol ethoxylate ether (40 ethoxylate groups/molecule) |
| Triton N-42 | nonylphenol ethoxylate ether (4 ethoxylate groups/molecule) |

I claim:

1. A hair dye composition, comprising:

a) one or more hair dyeing agents;

b) from 0.2 to 5 weight percent of at least three polyethoxylated urethanes, based on the total weight of the hair dye composition;

c) from 1.0 to 25 weight percent, based on the total weight of the hair dye composition, of at least one nonionic associative agent containing at least one hydrophilic group and at least one hydrophobic group which interacts with the polyethoxylated urethanes to provide thickening properties; and d) water;

wherein the polyethoxylated urethanes are a mixture of polyethoxylated urethanes comprising a first polyethoxylated urethane with at least two end groups, where each end group comprises a terminal isocyanate and a polyether; a second polyethoxylated urethane with at least two end groups, where each end group comprises a terminal isocyanate group and a non-functional group; and a third polyethoxylated urethane with at least two end groups, where one end group comprises a terminal isocyanate and a polyether and one other end group comprises a terminal isocyanate and a non-functional group; and wherein the viscosity of the hair dye composition at a shear rate of 0.3 rpm or less is at least 6000 centipoise, and the viscosity of the hair dye composition at a shear rate of greater than or equal to 30 rpm is less than or equal to 6000 centipoise.

2. A method of making the hair dye composition of claim 1, comprising:

a) forming a dye lotion part comprising one or more hair dyeing agents, and at least one first compound selected from the group consisting of polyethoxylated urethane, nonionic associative agent containing at least one hydrophilic group and at least one hydrophobic group, and combinations thereof;

b) forming a developer solution part comprising at least one oxidizing agent, water and at least one second compound selected from the group consisting of polyethoxylated urethane, nonionic associative agent containing at least one hydrophilic group and at least one hydrophobic group, and combinations thereof; and c) combining the dye lotion and the developer solution to form the hair dye composition;

wherein the polyethoxylated urethane is a mixture of polyethoxylated urethanes comprising a first polyethoxylated urethane with at least two end groups, where each end group comprises a terminal isocyanate and a polyether; a second polyethoxylated urethane with at least two end groups, where each end group comprises a terminal isocyanate group and a non-functional group; and a third polyethoxylated urethane with at least two end groups, where one end group comprises a terminal isocyanate and a polyether and one other end group comprises a terminal isocyanate and a non-functional group; and provided that when the parts of the multi-part hair dye composition are combined to form a combined hair dye composition, the combined hair dye composition comprises said mixture of polyethoxylated urethanes, and at least one nonionic associative agent containing at least one hydrophilic group and at least one hydrophobic group which interacts with the polyethoxylated urethanes to provide thickening properties; wherein the viscosity of the hair dye composition at a shear rate of 0.3 rpm or less is at least 6000 centipoise, and the viscosity of the hair dye composition at a shear rate of greater than or equal to 30 rpm is less than or equal to 6000 centipoise.

3. A multi-part hair dye composition, comprising:

a) a dye lotion part comprising one or more hair dyeing agents, and at least one first compound selected from the group consisting of a polyethoxylated urethane, nonionic associative agent containing at least one hydrophilic group and at least one hydrophobic group, and combinations thereof; and b) a developer solution part comprising at least one oxidizing agent, water, and at least one second compound selected from the group consisting of a polyethoxylated urethane, nonionic associative agent containing at least one hydrophilic group and at least one hydrophobic group, and combinations thereof;

wherein the polyethoxylated urethane is a mixture of polyethoxylated urethanes comprising a first polyethoxylated urethane with at least two end groups, where each end group comprises a terminal isocyanate and a polyether; a second polyethoxylated urethane with at least two end groups, where each end group comprises a terminal isocyanate group and a non-functional group; and a third polyethoxylated urethane with at least two end groups, where one end group comprises a terminal isocyanate and a polyether and one other end group comprises a terminal isocyanate and a non-functional group; and provided that when the parts of the multi-part hair dye composition are combined to form a combined hair dye composition, the combined hair dye composition comprises said mixture of polyethoxylated urethanes, and at least one nonionic associative agent containing at least one hydrophilic group and at least one hydrophobic group which interacts with the polyethoxylated urethanes to provide thickening properties; wherein the viscosity of the hair dye composition at a shear rate of 0.3 rpm or less is at least 6000 centipoise, and the viscosity of the hair dye composition at a shear rate of greater than or equal to 30 rpm is less than or equal to 6000 centipoise.

4. The composition of claim 1 or 3, wherein the nonionic associative agent has an average HLB of 15 or less, and has at least one hydrophobic group having from 6 to 30 carbon atoms.

5. The composition of claim 1 or 3, wherein the nonionic associative agent is selected from the group consisting of an alcohol ethoxylate, an alkylphenol ethoxylate, and combinations thereof.

6. A method of dyeing hair, comprising: applying the hair dye composition of claim 1 or 3 onto the hair.

7. A method of thickening a hair dye composition, comprising: combining one or more hair dyeing agents, water, from 0.2 to 5 weight percent of at least three polyethoxylated urethanes, and from 1.0 to 25 weight percent of at least one nonionic associative agent containing at least one hydrophilic group and at least one hydrophobic group which interacts with the polyethoxylated urethane to provide thickening properties to form the hair dye composition, wherein the polyethoxylated urethanes are a mixture of polyethoxylated urethanes comprising a first polyethoxylated urethane with at least two end groups, where each end group comprises a terminal isocyanate and a polyether; a second polyethoxylated urethane with at least two end groups, where each end group comprises a terminal isocyanate group and a non-functional group; and a third polyethoxylated urethane with at least two end groups, where one end group comprises a terminal isocyanate and a polyether and one other end group comprises a terminal isocyanate and a non-functional group; and wherein the viscosity of the hair dye composition at a shear rate of 0.3 rpm or less is at least 6000 centipoise, and the viscosity of the hair dye composition at a shear rate of greater than or equal to 30 rpm is less than or equal to 6000 centipoise.

8. The hair dye composition of claim 1, wherein the viscosity of the hair dye composition at a shear rate of 0.3 rpm or less is at least 12,000 centipoise, and the viscosity of the hair dye composition at a shear rate of greater than or equal to 30 rpm is less than or equal to 3000 centipoise.

9. The hair dye composition of claim 1, comprising from 5 to 20 weight percent, based on the total weight of the hair dye composition, of the nonionic associative agent.

10. The multi-part hair dye composition of claim 3, wherein the viscosity of the hair dye composition at a shear rate of 0.3 rpm or less is at least 12,000 centipoise, and the viscosity of the hair dye composition at a shear rate of greater than or equal to 30 rpm is less than or equal to 3000 centipoise.

11. The multi-part hair dye composition of claim 3, further comprising that when the nonionic associative agent has an HLB of 12 or less, the associative agent is added to the dye lotion or developer solution part not containing the polyethoxylated urethane.

12. The composition of claim 4, wherein the nonionic associative agent has an average HLB of 12 or less.

* * * * *